United States Patent [19]

Hauptmann

[11] Patent Number: 5,683,425
[45] Date of Patent: Nov. 4, 1997

[54] HEART PACEMAKER WITH IMPROVED DETECTION OF ELECTRICAL SIGNALS

[75] Inventor: Werner Hauptmann, Munich, Germany

[73] Assignee: Pacesetter AB, Solna, Sweden

[21] Appl. No.: 571,189

[22] Filed: Dec. 12, 1995

[30] Foreign Application Priority Data

Dec. 12, 1994 [DE] Germany .................. 44 44 144.4

[51] Int. Cl.⁶ .................................................. A61N 1/36
[52] U.S. Cl. .................. 607/9; 128/708; 128/901
[58] Field of Search ........................ 607/9; 128/696, 128/697, 708, 901

[56] References Cited

U.S. PATENT DOCUMENTS 4,385,634  5/1983  Bowen ........................ 128/736 X
4,616,659 10/1986 Prezas et al. ................. 128/706
5,010,887  4/1991  Thornander ................... 128/708
5,211,179  5/1993  Haberl et al. ................. 128/702

*Primary Examiner*—Jeffrey R. Jastrzab
*Attorney, Agent, or Firm*—Hill, Steadman & Simpson

[57] ABSTRACT

A heart pacemaker with improved detection of electrical signals which are used for triggering pacemaker functions, has a detection circuit for registering intracardial heart signals in which certain noise signals having a generally chromatic spectrum are superimposed on the signals to be detected, the detection circuit undertaking an adaptive, non-linear noise filter of those intracardial heart signals for converting the spectrum of the noise signals into an essentially white spectrum. The signals filtered by the non-linear noise filtering are supplied to a matched filter wherein correlation of these signals with a sought signal pattern takes place.

11 Claims, 3 Drawing Sheets

HEART PACEMAKER WITH IMPROVED DETECTION OF ELECTRICAL SIGNALS

BACKGROUND OF THE INVENTION

1. Field of the Invention

The present invention is directed to a heart pacemaker having a detection system (sensing circuit) which achieves improved detection of electrical cardiac signals.

2. Description of the Prior Art

The detection system, also referred to as the "sensing circuit," represents one of the critical and most important components of a heart pacemaker. This system has the task of continuously monitoring the electrical activity of the heart via the pacemaker electrodes at a time between the pacemaker pulses that are emitted. The actions of the heart pacemaker are then controlled dependent on the observed activity, i.e. generator pulses are triggered or suppressed.

Even though this is a critical component in the function of the overall system, only very simple methods and devices for signal recognition and noise suppression are employed in currently available heart pacemakers. Only simple threshold discriminators are often utilized for the recognition of a QRS complex; in some devices, at least the rise time of the signal is additionally interpreted. Simple band-pass filters are sometimes employed for noise reduction in order to suppress noise signals that have a high amplitude but which lie in a different frequency range. A number of known devices and the basic technical knowledge available to a person skilled in the art in this field are described, for example, in Moses, H. W. et al., "A Practical Guide to Cardiac Pacing", Little, Brown and Company, Boston, 1991, 3rd ed; Gülker H. et al., "Leitfaden zur Therapie der Herzrhythmusstörungen", pp. 196–231, de Gruyter, 1992, ". Aufl; Haykin, S., "Adaptive Filter Theory", Prentice Hall Intl, Inc., Englewood Cliffs, 1991; and van Trees, H. L., "Detection, Estimation, and Linear Modulation Theory", Wiley & Sons, New York, 1968

These procedures, however, are inadequate for various reasons. In the case of a detection of events with the assistance of signal amplitudes or rise times by themselves, an existing, weaker QRS signal may not be recognized, whereas, a strong noise pulse may be interpreted as a heart signal. Further, the region of the frequency band wherein the QRS complex lies is different in different patients; it even shifts for various heartbeats of an individual patient. Due to the extremely simple methods that are employed, misbehavior and functional disturbances due to noise signals, crosstalk or non-detection of weak electrical heart activity occasionally occur in currently realized systems.

SUMMARY OF THE INVENTION

An object of the present invention is to enhance the performance capability and ruggedness of the detection system of a heart pacemaker. In general, this object is achieved in a heart pacemaker having a processing system for improved detection of defined signal events, also serving for improved suppression of internal and external disturbing and noise influences. More specifically, a heart pacemaker with improved detection of electrical signals is disclosed having means for registering intracardial heart signals in which certain noise signals having a generally chromatic spectrum are superimposed on the signals to be detected, means for adaptive, non-linear noise filtering of these intracardial heart signals for converting the spectrum of the noise signals into an essentially white spectrum, as well as means for matched filtering (MF) of the signals filtered by the non-linear noise filtering by correlating these signals with a signal pattern. Finally, an output quantity is generated whose amplitude is a criterion for the presence of this signal pattern in the heart signal. By contrast to known heart pacemakers, the invention employs an adaptive, non-linear noise filter for converting the spectrum of the noise signals into an essentially white spectrum. As a result, the detection of certain signal patterns is significantly improved with the assistance of matched filters since these matched filters perform optimally only under the precondition that the noise spectrum is essentially white.

In a preferred embodiment of the invention, the generated output quantity is converted into a binary quantity by means of a threshold decision. As a result, the binary quantity can be directly employed for the control of further heart pacemaker functions, for example with the assistance of digital circuits suitable therefor. In an embodiment of the invention, this binary quantity can be employed for generating a trigger pulse that is employed for controlling heart pacemaker functions, and which is emitted as soon as the output quantity upwardly exceeds a predetermined threshold.

In an embodiment of the invention, the trigger signal is employed for extracting a sample of a sought signal pattern from the intracardial heart signal. This sample is subsequently employed for chronological adaptation of the signal pattern.

The invention is particularly suited for the detection of the QRS complex in the intracardial heart signal.

DESCRIPTION OF THE PREFERRED EMBODIMENTS

The goal of the invention is to enhance the performance capability and ruggedness of the detection system of a heart pacemaker by means of a processing system not only employed for improved detection of defined signal events, but also for improved suppression of internal and external noise and disturbing influences.

One of the principal functions of the detection system of a heart pacemaker is the constant, reliable recognition of the QRS complex generated by the heart. Dependent on whether such a QRS signal was received, a triggering or enabling of the emission of a pulse for the stimulation of the heart from the pulse generator of the heart pacemaker ensues shortly thereafter. The reliable and faultless function of the detector is thus directly dependent on whether

- a predetermined, well-defined signal event is always reliably recognized when it appears, and whether
- all other signal events, even if they have high energy or similarity to the sought signal event, are recognized as noise signals and are thus suppressed.

For example, the QRS complex or a defined pathological heartbeat pattern may be the defined signal event in this context. Typical noise signals in the context of the present invention are, for example, external disturbances or internal crosstalk given two-channel systems. A reliable decision of the detector is of considerable significance for the reliable functioning of the heart pacemaker. If, for example, a QRS signal is not recognized even though it was present, the heart pacemaker injects an event into the heart's electrical system that is already naturally occurring. When, by contrast, a QRS signal is identified as being present even though it is only an external disturbance and no natural stimulation of the heart was present, the emission of the heart pacemaker pulse is suppressed—no heartbeat ensues. Life-threatening disturbances in heart rhythm can occur in both instances.

Figure 1:
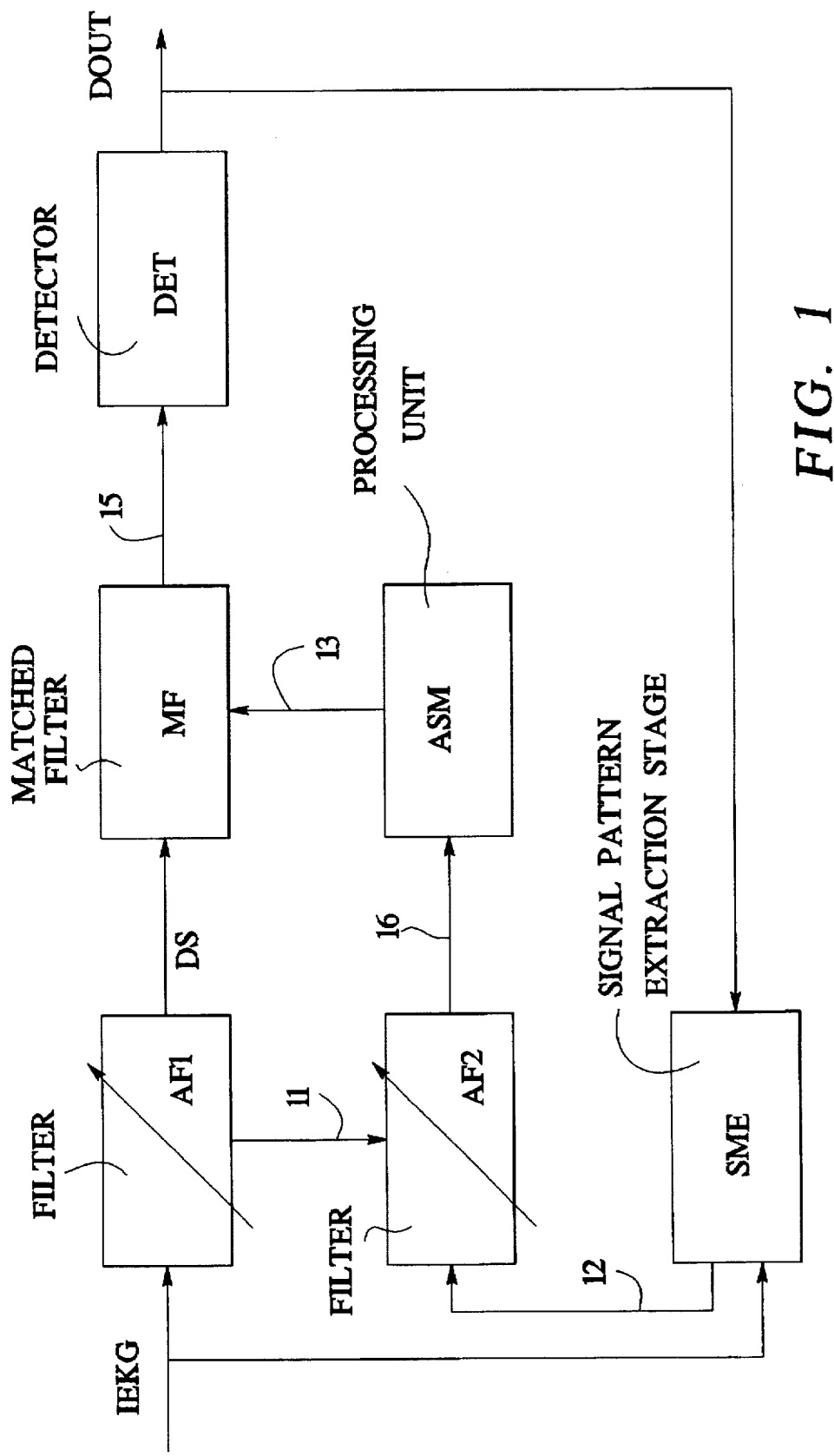
FIG. 1 is a block circuit diagram of the relevant components of a heart pacemaker detection system constructed in accordance with the principles of the present invention for adaptive detection of specific signal events with the assistance of matched filters MF, with reference to the example of the QRS complex.

Since the faultless detection of the QRS complex is the most important task of the detection system of the heart pacemaker, the functioning of the signal detection in the inventive system for the case of QRS recognition shall be set forth below. On the basis of the description of the invention provided herein, however, those skilled in the art is able without further difficulty to employ the invention for the detection of other signal events as well, for example defined pathological heartbeat patterns. The detection method disclosed herein and provided for processing intracardial heart signals is based on the linkage of approaches from classical signal processing (matched filter, LMS algorithm) with approaches from the field of neural networks (non-linear, adaptive noise filter). FIG. 1 schematically shows the structure of an inventive processing system for adaptive signal detection.

The input signal of the detector system is referred to as the intracardial electrocardiogram IEKG that is continuously observed via the heart pacemaker electrodes. The general goal in the context of signal detection is that of recognizing the signal event s(t) in the received signal x(t) that is additively superimposed by the noise n(t), i.e.

$$x(t)=s(t)+n(t) \quad (1)$$

In the case of recognizing a heartbeat in the IEKG, the signal s(t) represents the QRS complex and the noise n(t) represents all other components of the EKG, including the P-waves and T-waves, the noise of the circuits and instruments as well as disturbances due to muscle activity and other events. In the context of the IEKG signal, one has some prior knowledge about the relevant signal event in the form of a typical QRS signal pattern (template). Since the actual shape of the QRS signal, however, can differ between different patients, and can also be subject to chronological fluctuations in the same patient, an automatic adaptation of the momentarily (currently) valid signal pattern is also undertaken in the inventive detection system. This adaptation shall be set forth below. The prior knowledge about the signal event is utilized by the inventive signal detector by employing a matched filter MF whose impulse response is matched to the sought signal event (signal pattern). A continuous correlation between the incoming signal and the test pattern ensues. The filter MF can be realized by a digital FIR (finite impulse response), filter that has the impulse response $h(t)=s(t-t_0)$, so that the signal-to-noise ratio at the output of the filter MF is maximum when x(t) is applied to the input. The signal-to-noise ratio (SNR) is thereby defined by $$SNR = \frac{|y_s(t_0)|}{\sqrt{E\{y_n^2\}}} \quad (2)$$

In this equation, the response of the filter to the signal part is $$y_s(t_0)=s(t)*h(t) \quad (3)$$

as a result of the convolution of the signal (for example, of the QRS complex) with the pulse response of the filter MF. The filter response to the noise part similarly is $$y_n(t_0)=n(t)*h(t) \quad (4)$$

The described, matched filter MF only behaves as an optimum detector when the disturbing signal, i.e. the noise signal n(t), is a stationary white noise process. This, however, is not the case in the detection of the QRS complex. On the contrary, a chromatic noise signal that contains parts of the EKG signal, for example the P-wave and T-wave, the noise of the instruments, and disturbances produced by muscle activities, is superimposed on the useful signal of interest. These components are often correlated, highly non-linear and non-stationary noise processes, referred to as chromatic noise. In order to be able to apply the inventive detection method with the matched filter MF in this case, a pre-processing by a "whitening" filter formed by a first adaptive filter AF1 (a noise filter or a decorrelation filter) with which the correlated parts of the noise are suppressed, must ensue before the correlation with the test pattern.

Figure 2:
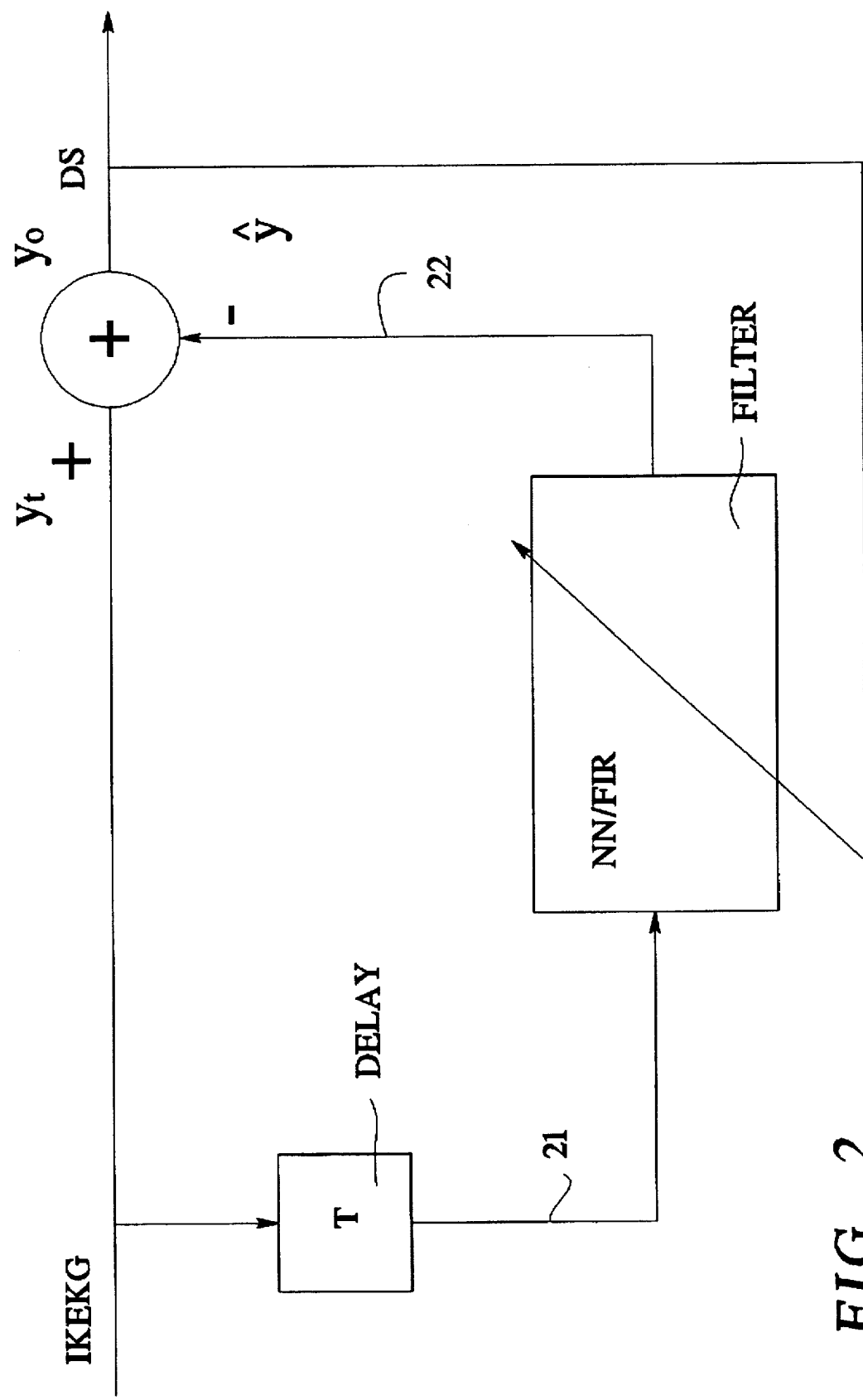
FIG. 2 is a block circuit diagram of an adaptive, neural noise filter NN/FIR, as preferably employed in conjunction with the invention.

An autoregressive model (AR model) usually forms the basis for modeling the superimposed, correlated noise process in the filter AF1. Correspondingly, the inventive noise filter AF1 can thus be constructed as a linear adaptive filter whose coefficients are set according to the calculated AR parameters. Given the problem present herein, the background noise processes, however, are highly non-linear and the use of such a linear filter is therefore not especially effective. For improved noise process modeling, the invention therefore provides a method of signal filtering that is based on the principle of a neural network. To that end, the standard, linear adaptive decorrelation filter is replaced by an adaptive, non-linear noise filter. FIG. 2 schematically shows the block circuit diagram of such a neural filter NN that, except for the actual processing stage NN/FIR, corresponds to that of a conventional linear, adaptive filter.

Figure 4:
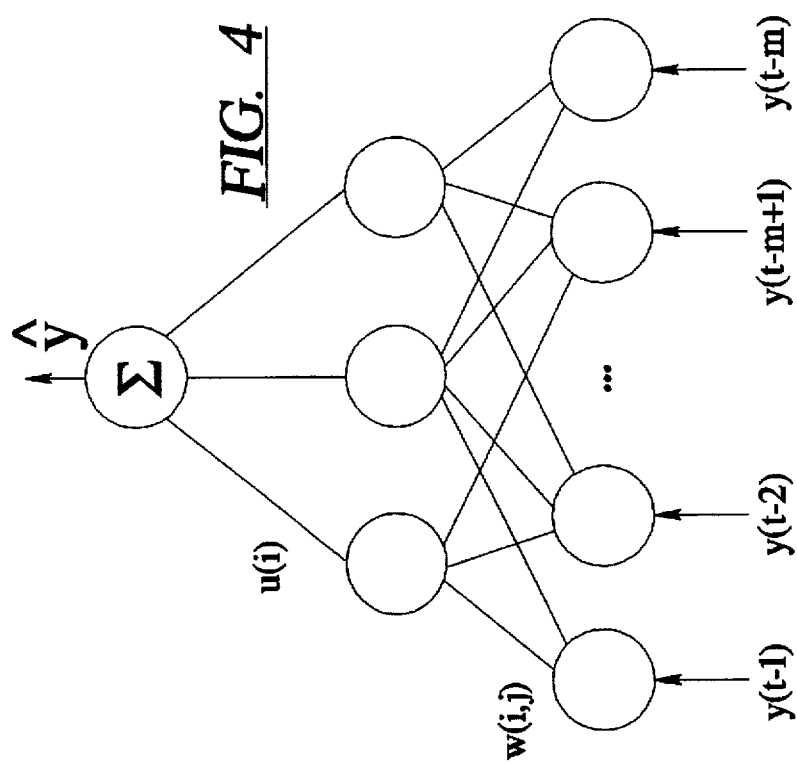
FIG. 4 shows a schematic illustration of a non-linear, adaptive, neural filter NN/FIR as preferably employed in conjunction with the invention.
Figure 3:
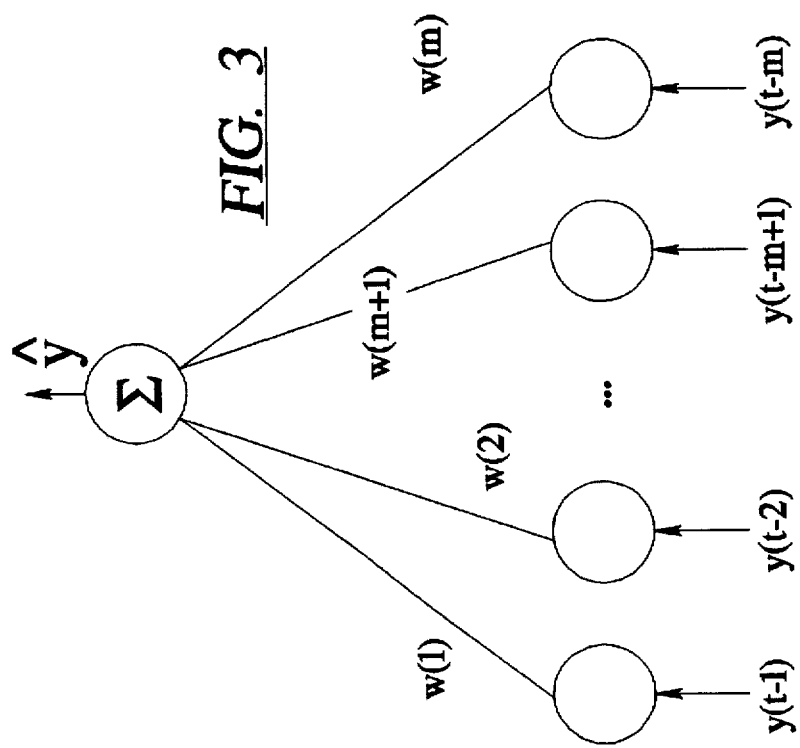
FIG. 3 schematically shows the structure of a conventional, linear adaptive FIR filter.

The structure of this processing stage NN/FIR of the neural FIR filter is again schematically shown in detail in FIG. 4 and can thus be compared to the corresponding structure of a conventional, linear adaptive filter as shown in FIG. 3. The basic structure of the neural adaptive filter NN is composed of three layers: an input layer, an output layer and a hidden layer. The non-linear adaptive, neural filter can be imagined as well as an expansion of the linear filter by a hidden layer. This layer is composed of non-linear processing nodes that supply the intermediate results $$z_i = f\left(\sum_{j=1}^{M} w_{ij} y_{t-j} + b_j\right) \quad (5)$$

at their outputs. A sigmoid function is used as activation function f( ). The weightings are referenced $w_{ij}$, these connecting the input nodes to the nodes of the hidden layer; the quantities $b_{ij}$ are the offset values. The output of the processing stage NN/FIR of the neural filter is a linear combination of the output values of the hidden layer. The quantity $y_0$ as the modeling error at the output of the overall decorrelation filter as shown in FIG. 2 is thus $$y_0 = y_t - \hat{y} = y_t - \sum_{i=1}^{q} u_i z_{t-i} = y_t - \sum_{i=1}^{q} u_i f\left( \sum_{j=1}^{M} w_{ij} y_{t-j} + b_j \right) \quad (6)$$

the weightings between the hidden layer and the output node being referenced $u_i$. The reduction of this modeling error is the training objective for the training of the neural network that is implemented continuously according to the so-called "back propagation" technique. The network has only one output that supplies the modeled noise process; the number of nodes of the hidden layer is variable. The number of inputs of the neural network corresponds to the order of the filter and must be correspondingly selected. Those skilled in the art are able to select the filter arrangement, and thus, the number of inputs appropriate for a particular purpose using their expertise.

The continuous adaptation to the current noise process and the non-linearity of the neural signal filter AF1 allow a more exact modeling of the underlying signal characteristic. The correlated noise part of the signal x(t) at the input of the filter AF1 is thus decorrelated in the filter AF1, i.e. it has a white spectral characteristic after the filter AF1, and can be supplied to the input of the following, matched filter MF.

The basic processing steps of the adaptive detection algorithm shall be set forth again in summary below with reference to the block circuit diagram (FIG. 1):

The electrical signal that is picked up by the heart pacemaker probe, the IEKG, is supplied to the adaptive, non-linear neural filter AF1 via the detector input. This filter AF1 models the momentary noise process of the signal and correspondingly adapts its weightings and filter coefficients. After a short adaptation time, a signal DS is present at the output of the filter AF1 that has a substantially white spectral characteristic.

This signal is forwarded to the matched filter MF whose filter coefficients are preset according to the signal event to be detected (for example, the QRS complex). A correlation of the incoming signal with the sought signal pattern ensues in the matched filter MF, whose analog output increases with increasing correlation with the sought signal. A maximum or close to maximum value arises on line 15 at the output of the matched filter MF only when a corresponding QRS complex is detected. A simple threshold decision is made in the following QRS detector DET and a short trigger pulse is forwarded to the detector output as soon as a predetermined threshold is upwardly transgressed. This trigger pulse can be used for generating or suppressing a heart pacemaker pulse.

In a preferred embodiment of the invention, the sought signal pattern is also continuously adapted over time in addition to the adaptation of the filter AF1. As a result thereof, an adaptation to chronologically variable signal patterns (for example chronologically varied QRS complexes) is possible. Since the exact course of a QRS signal is subject to chronological changes, this enables a constantly high recognition rate of the detector. An individual adjustment adapted to the patient is thus also enabled. To that end, the input signal is supplied to a signal pattern extraction stage SME. The current shape (envelope) of the QRS signal is extracted here from the constantly supplied original signal IEKG with the assistance of the trigger signal at the output of the detector DET at adjustable intervals, supplied on line 12 to another adaptive filter AF2 that is identical to the filter AF1 at the detector input, wherein the extracted signal is decorrelated. To ensure identical filter parameters for filters AF1 and AF2 the currently valid filter coefficients of AF1 are forwarded to filter AF2 via line 11. In every update the extracted signal pattern is emitted to a signal buffer ASM via line 16 where N signal patterns from the preceding updates are stored and the current signal pattern that is used for the matched filtering in the filter MF (supplied via line 13) is calculated in the processing unit ASM by averaging over these N most recent patterns according to the equation $$QRS = \frac{1}{N} \sum_{i=1}^{N} QRS(t) \quad (7)$$

In the updating, the oldest signal pattern is erased and the new, current QRS pattern is calculated according to this relationship. Dependent on the selection of the number of past signal patterns N which are used, a determination can be made as to how large the influence of the most recent signal event should be.

It will be clear to those skilled in the art on the basis of the present specification that the invention is not exclusively limited to the detection of the QRS complex. Other characteristic signal events can be detected with the assistance of the invention and the patient can thus be warned, for example given recognition of dangerous signal events.

Although modifications and changes may be suggested by those skilled in the art, it is the intention of the inventors to embody within the patent warranted hereon all changes and modifications as reasonably and properly come within the scope of their contribution to the art.

I claim as my invention:

1. In a heart pacemaker supplied with electrical signals obtained from a heart, the improvement of a system for detecting said electrical signals comprising:

means for acquiring electrical intracardial heart signals containing a signal of interest and having noise with a substantially chromatic spectrum superimposed on said signal of interest;

means for adaptive, non-linear filtering of said intracardial heart signals for converting the spectrum of the noise into a substantially white spectrum, thereby producing filtered signals; and means for matched filtering of said filtered signals by correlating said filtered signals with a signal pattern corresponding to said signal of interest and generating a matched filter output having an amplitude indicative of the presence of said signal pattern in said filtered signal.

2. The improvement of claim 1 further comprising means for comparing said output to a threshold for generating a binary signal having a high level when said output exceeds said threshold.

3. The improvement of claim 2 further comprising means for triggering a pacemaker function when said output exceeds said threshold.

4. The improvement of claim 3 wherein said means for triggering a pacemaker function includes means for generating a trigger signal, and said improvement comprising means for extracting a sample of said signal pattern from said intracardial heart signal at a time coinciding with said trigger signal, and for chronologically adapting said means for matched filtering dependent on said sample.

5. The improvement of claim 1 wherein said electrical intracardial heart signals contain a QRS complex, and wherein said means for matched filtering comprises means for correlating said filtered signal with a QRS complex signal pattern.

6. The improvement of claim 1 wherein said means for adaptive, nonlinear filtering comprises a neural network finite impulse response filter.

7. A method for detecting said electrical signals in a heart pacemaker comprising the steps of:
  acquiring electrical intracardial heart signals containing a signal of interest and having noise with a substantially chromatic spectrum superimposed on said signal of interest;
  adaptively, non-linearly filtering said intracardial heart signals for converting the spectrum of the noise into a substantially white spectrum, thereby producing filtered signals; and
  matched filtering said filtered signals by correlating said filtered signals with a signal pattern corresponding to said signal of interest and generating a matched filter output having an amplitude indicative of the presence of said signal pattern in said filtered signal.

8. The method of claim 7 comprising the additional steps of comparing said output to a threshold and generating a binary signal having a high level when said output exceeds said threshold.

9. The method of claim 8 comprising the additional step of triggering a pacemaker function when said output exceeds said threshold.

10. The method of claim 9, wherein the step of triggering a pacemaker function includes generating a trigger signal, and said method comprising the further steps of extracting a sample of said signal pattern from said intracardial heart signal at a time coinciding with said trigger signal, and chronologically adapting said matched filter dependent on said sample.

11. The method of claim 7 wherein said electrical intracardial heart signals contain a QRS complex, and wherein the step of matched filtering comprises correlating no filtered signal with a QRS complex signal pattern.

* * * * *